United States Patent [19]

Ackermann et al.

[11] 4,331,682
[45] May 25, 1982

[54] CYCLOPROPANECARBOXYLIC ACID-α-HALOETHYNYL-M-PHENOXYBENZYL ESTERS AND THEIR USE FOR COMBATING INSECT PESTS

[75] Inventors: Peter Ackermann, Reinach; Jozef Drabek, Oberwil; Saleem Farooq, Ettingen; Laurenz Gsell, Basel; Odd Kristiansen, Möhlin; Rudolf Wehrli, Rheinfelden, all of Switzerland

[73] Assignee: Ciba-Geigy Corporation, Ardsley, N.Y.

[21] Appl. No.: 239,868

[22] Filed: Mar. 2, 1981

[30] Foreign Application Priority Data

Mar. 14, 1980 [CH] Switzerland ........................ 2014/80
Sep. 16, 1980 [CH] Switzerland ........................ 6928/80

[51] Int. Cl.³ .................... C07C 67/943; A01N 53/00
[52] U.S. Cl. ................................ 424/305; 560/124; 568/637
[58] Field of Search ...................... 560/124; 424/305

[56] References Cited

U.S. PATENT DOCUMENTS 4,225,516 9/1980 Ackermann ........................ 560/124
4,231,932 11/1980 Martel ................................ 560/124

FOREIGN PATENT DOCUMENTS 2742546 9/1977 Fed. Rep. of Germany .

Primary Examiner—Michael L. Shippen
Attorney, Agent, or Firm—Frederick H. Rabin

[57] ABSTRACT

Cyclopropanecarboxylic acid-α-haloethynyl-m-phenoxybenzyl esters of the formula

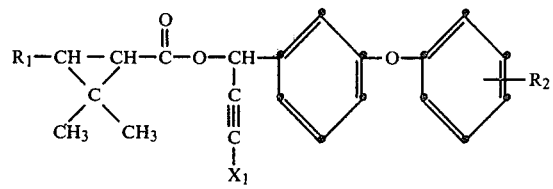

wherein
$R_1$ is

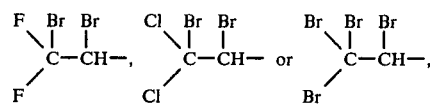

$R_2$ is hydrogen, fluorine, chlorine, bromine, methyl, trifluoromethyl or methoxy, and
$X_1$ is halogen, processes for producing them, and their use for combating insect pests.

8 Claims, No Drawings

CYCLOPROPANECARBOXYLIC ACID-α-HALOETHYNYL-M-PHENOXYBENZYL ESTERS AND THEIR USE FOR COMBATING INSECT PESTS

The present invention relates to cyclopropanecarboxylic acid-α-haloethynyl-m-phenoxybenzyl esters, to processes for producing them, and to their use for combating insect pests.

The cyclopropanecarboxylic acid-α-haloethynyl-m-phenoxybenzyl esters according to the invention have the formula

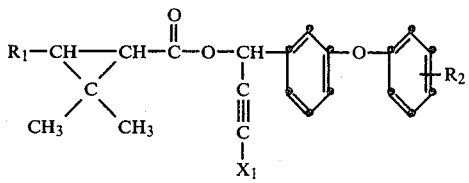
(I)

wherein
$R_1$ is

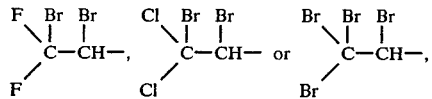

$R_2$ is hydrogen, fluorine, chlorine, bromine, methyl, trifluoromethyl or methoxy, and
$X_1$ is halogen.

By halogen is meant fluorine, chlorine, bromine or iodine, especially however bromine or iodine. Compounds of the formula I of particular importance on account of their action are those wherein
$R_1$ is

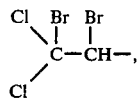

$R_2$ is hydrogen, fluorine, chlorine, bromine or trifluoromethyl, and
$X_1$ is bromine or iodine.

More especially of importance however are compounds of the formula I wherein
$R_1$ is

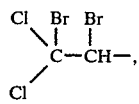

$R_2$ is hydrogen or fluorine, and
$X_1$ is bromine or iodine.

The compounds of the formula I are produced by methods known per se, for example as follows:

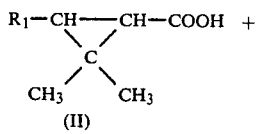
(II)

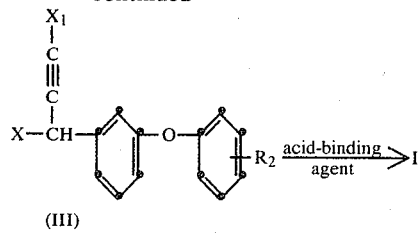
(III)

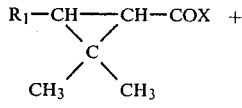
(2)
(IV)

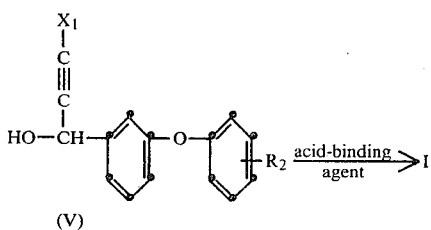
(V)

(3)
(II)

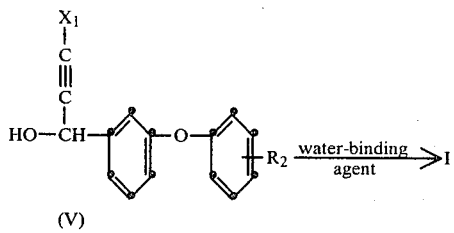
(V)

(4)
(VI)

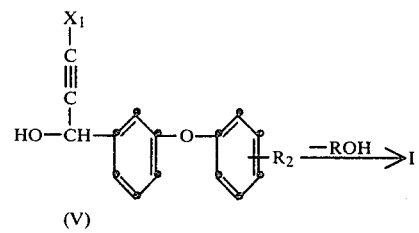
(V)

In the formulae II to VI, the symbols $R_1$, $R_2$ and $X_1$ have the meanings defined under the formula I.

X in the formulae III and IV is a halogen atom, especially chlorine or bromine; and R in the formula VI is $C_1$–$C_4$-alkyl, particularly methyl or ethyl. Suitable acid-binding agents for the processes 1 and 2 are in particular tertiary amines, such as trialkylamine and pyridine, also hydroxides, oxides, carbonates and bicarbonates of alkali metals and alkaline-earth metals, as well as alkali metal alkoholates, for example potassium tert-butylate and sodium methylate. The water-binding agent used for the process 3 can be for example dicyclohexylcarbodiimide. The processes 1 to 4 are performed at a reaction temperature of between −10° and 120° C., usually between 20° and 80° C., under normal or elevated pressure, and preferably in an inert solvent or diluent. Suitable solvents or diluents are for example: ethers and ethereal compounds, such as diethyl ether, dipropyl ether, dioxane, dimethoxyethane and tetrahydrofuran; amides, such as N,N-dialkylated carboxylic acid amides; aliphatic, aromatic as well as halogenated hydrocarbons, especially benzene, toluene, xylenes, chloroform and chlorobenzene; nitriles such as acetonitrile; dimethyl sulfoxide, and ketones such as acetone and methyl ethyl ketone.

The starting materials of the formulae II, IV and VI are known, or they can be produced by methods analogous to known methods. The starting materials of the formulae III and V are novel. They are produced in a manner analogous to that described in Tetrahedron Letters, Vol. 34, pp. 1449–1452 (1978) (cp. also Example 1A).

If homogeneous optically active starting materials are not used in producing the compounds of the formula I, these compounds are obtained as mixtures of various optically active isomers. The different isomeric mixtures can be separated by known methods into the individual isomers. By the term 'compounds of the formula I' are meant both the individual isomers and the mixtures thereof.

The compounds of the formula I are suitable for combating various animal and plant pests.

The compounds of the formula I are particularly suitable for combating insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as members of the order Acarina, such as phytopathogenic mites, and zooparasitic ticks.

In particular, compounds of the formula I are suitable for combating insects that damage plants, especially insects that damage plants by eating, in crops of ornamental plants and productive plants, particularly in cotton crops (for example against Spodoptera littoralis and Heliothis virescens), and in vegetable crops (for example against Leptinotarsa decemlineata and Myzus persicae). Active substances of the formula I have a very favourable action also against flies, such as Musca domestica, and against mosquito larvae.

The acaricidal and insecticidal action can be substantially broadened and adapted to suit given circumstances by the addition of other insecticides and/or acaricides. Suitable additives are for example: organic phosphorus compounds, nitrophenols and derivatives thereof, formamidines, ureas, other pyrethrin-like compounds as well as carbamates and chlorinated hydrocarbons.

Compounds of the formula I are combined particularly advantageously also with substances having a synergistic or intensifying effect on pyrethroids. Examples of compounds of this type are, inter alia: piperonyl-butoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-octyl-sulfinyl)-propyl)-benzene.

The compounds of the formula I can be used in a known manner either in an unmodified form or, together with the auxiliaries customarily used in formulation practice, in the form of preparations, for example emulsion concentrates, suspension concentrates, directly sprayable solutions or dilutable solutions, diluted emulsions, wettable powders, soluble powders, dusts or granulates, and also superfine encapsulations in polymeric substances, and the like. The form of application, such as spraying, atomising, dusting, scattering or pouring, is governed entirely by the purpose of application. It is to be ensured however in this respect that the biological behavior of the active substances of the formula I is not disadvantageously affected by the method of application, or by the type and amount of auxiliaries used for producing the preparation.

The preparations are produced in a known manner, for example by the intimate mixing and/or grinding of the active substances with extenders, such as with solvents or solid carriers, and optionally with the use of surface-active substances (tensides). The solvents used can be: aromatic hydrocarbons, preferably the fractions $C_8$ to $C_{12}$, i.e. xylene mixtures or substituted naphthalenes, aliphatic hydrocarbons, such as cyclohexane or paraffins, alcohols and glycols, as well as ethers and esters thereof, strongly polar solvents, such as dimethylsulfoxide or dimethylformamide, and also water. The solid carriers used, for example for dusts and dispersible powders, are mostly natural mineral fillers, such as calcite, talcum, kaolinite, montmorillonite and attapulgite. In order to improve the physical properties, it is also possible to use highly dispersed silicic acids or highly dispersed absorbent polymers. Suitable granulated adsorptive carriers are porous types, for example pumice, broken brick, sepiolite and bentonite; and suitable nonsorbent carriers are for example calcite or sand. There can also be used a great number of granulated materials of inorganic or organic nature, such as in particular dolomite, extending to ground plant residues.

Suitable surface-active substances are, depending on the polarity of the active substance of the formula I to be formulated, nonionic, cation-active and/or anion-active tensides having good emulsifying, dispersing and wetting properties; and by tensides are also meant tenside mixtures.

Suitable cation-active tensides are for example: quaternary ammonium compounds, such as cetyltrimethylammonium bromide. Suitable anion-active tensides are for example: soaps, salts of aliphatic monoesters of sulfuric acid, such as sodium lauryl sulfate, salts of sulfonated aromatic compounds, for example sodium dodecylbenzenesulfonate, sodium-, calcium- and ammonium-lignin sulfonate, butylnaphthalene sulfonate or a mixture of the sodium salts of diisopropyl- and triisopropylnaphthalene sulfonate. Suitable nonionogenic tensides are for example the condensation products of ethylene oxide with fatty alcohols, for example oleyl alcohol or cetyl alcohol, or with alkylphenols, such as octylphenol, nonylphenol and octylcresol. Other nonionic agents are the partial esters derived from long-chain fatty acids and hexite anhydrides, and the condensation products of these partial esters with ethylene oxide, and lecithins.

The nonionic, anion-active and cation-active tensides commonly used in formulation practice are described in, inter alia, the following publication: "Mc Cutcheon's Detergents and Emulsifiers Annual", MC Publishing Corp., Ringewood, N.J., 1979.

The formulated compositions contain as a rule 0.1 to 99%, particularly 0.1 to 95%, of active substance of the formula I, and 0 to 25% of a tenside, as well as 1 to 99.9% of a solid or liquid additive.

The compositions can also contain further additives, such as stabilisers, defoaming agents, viscosity regulators, binders, adhesives, as well as fertilisers or other active substances for producing special effects.

The active substances of the formula I can be produced for example as follows (values in % by weight):

FORMULATION EXAMPLES FOR LIQUID ACTIVE SUBSTANCES OF THE FORMULA I

| Emulsion concentrates | |
|---|---|
| (a) active substance | 20% |
| calcium dodecylbenzenesulfonate | 5% |
| castor oil-polyglycol ether (36 mols of ethylene oxide) | 5% |
| xylene mixture | 70%; |
| (b) active substance | 40% |
| calcium dodecylbenzenesulfonate | 8% |
| tributylphenol-polyglycol ether (30 mols of ethylene oxide) | 12% |
| cyclohexanone | 15% |
| xylene mixture | 25%; |
| (c) active substance | 50% |
| tributylphenol-polyglycol ether | 4.2% |
| calcium dodecylbenzenesulfonate | 5.8% |
| cyclohexanone | 20% |
| xylene mixture | 20%. |

Emulsions of any required concentration can be produced from concentrates of this type by dilution with water.

| Solutions | |
|---|---|
| (a) active substance | 80% |
| ethylene glycol monomethyl ether | 20%; |
| (b) active substance | 10% |
| polyethylene glycol 400 | 70% |
| N-methyl-2-pyrrolidone | 20%; |
| (c) active substance | 5% |
| epoxidised vegetable oil | 1% |
| ligroin (boiling limits 160–190° C.) | 94%; |
| (d) active substance | 95% |
| epoxidised vegetable oil | 5%. |

These solutions are suitable for application in the form of drops as small as possible.

| Granulates | |
|---|---|
| (a) active substance | 5% |
| kaolin (0.2–0.8 mm) | 94% |
| highly dispersed silicic acid | 1%; |
| (b) active substance | 10% |
| attapulgite | 90%. |

The active substance is dissolved in methylene chloride, the solution is sprayed onto the carrier, and the solvent is subsequently evaporated off in vacuo.

| Dusts | |
|---|---|
| (a) active substance | 2% |
| highly dispersed silicic acid | 1% |
| talcum | 97%; |
| (b) active substance | 5% |
| highly dispersed silicic acid | 5% |
| kaolin (finely divided) | 90%. |

Ready-for-use dusts are obtained by the intimate mixing of the carriers with the active substance.

FORMULATION EXAMPLES FOR SOLID ACTIVE SUBSTANCES OF THE FORMULA I

| Wettable powders | |
|---|---|
| (a) active substance | 20% |
| sodium lignin sulfonate | 5% |
| sodium lauryl sulfate | 3% |
| silicic acid | 5% |
| kaolin | 67%; |
| (b) active substance | 60% |
| sodium lignin sulfonate | 5% |
| sodium diisobutylnaphthalenesulfonate | 6% |
| octylphenol polyglycol ether (7–8 mols of ethylene oxide) | 2% |
| highly dispersed silicic acid | 27%. |

The active substance is well mixed with the additives and the mixture is thoroughly ground in a suitable mill. Wettable powders which can be diluted with water to give suspensions of the desired concentration are obtained.

| Emulsion concentrate | |
|---|---|
| active substance | 10% |
| octylphenol polyglycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50%. |

Emulsions of any required concentration can be obtained from this concentrate by dilution with water.

| Dusts | |
|---|---|
| (a) active substance | 5% |
| talcum | 95%; |
| (b) active substance | 8% |
| kaolin (finely divided) | 92%. |

Dusts which are ready for use are obtained by mixing the active substance with the carriers, and grinding the mixture in a suitable mill.

| Extruder granulate | |
|---|---|
| active substance | 10% |
| sodium lignin sulfonate | 2% |
| carboxymethylcellulose | 1% |
| kaolin (finely divided) | 87%. |

The active substance is mixed and ground with the additives, and the mixture is subsequently moistened with water. The mixture is extruded and then dried in a stream of air.

| Coated granulate | |
|---|---|
| active substance | 3% |
| polyethylene glycol | 3% |
| kaolin (0.3–0.8 mm) | 94%. |

The finely ground active substance is uniformly applied, in a mixer, to the kaolin moistened with polyethylene glycol. Non-dusty coated granulates are obtained in this manner.

| Suspension concentrate | |
| --- | --- |
| active substance | 40% |
| ethylene glycol | 10% |
| nonylphenol polyglycol ether (15 mols of ethylene oxide) | 6% |
| sodium lignin sulfonate | 10% |
| carboxymethylcellulose | 1% |
| formalin (37% formaldehyde solution) | 0.2% |
| silicone oil in the form of a 75% emulsion | 0.8% |
| mains water | 32% |

The finely ground active substance is intimately mixed with the additives. There is thus obtained a suspension concentrate from which can be produced, by dilution with water, suspensions of the concentration required.

EXAMPLE 1

(A) 0.1 mol of methyl lithium dissolved in 50 ml of ether is added dropwise, within 20 minutes at −50° to −60° C. under argon, to 10 g of α-ethynyl-m-phenoxybenzyl alcohol in 500 ml of ether. After a further 10 minutes, 5.63 g of iodine dissolved in 100 ml of ether are added dropwise, and stirring is maintained at room temperature for 10 hours. 2 ml of isopropanol are slowly added dropwise, and 20 ml of saturated ammonium chloride solution are then added. The ether phase is washed with saturated sodium chloride solution and dried over magnesium sulfate. The solvent is removed and the residue is chromatographed on silica gel by means of ether/hexane (1:2). The product obtained is the compound of the formula

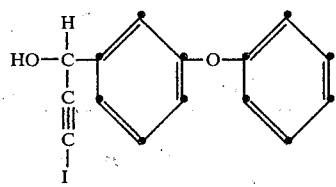

$n_D^{20°} = 1.6237$

NMR spectrum (60 MHz) in CDCl$_3$/TMS
δ3.1:d 1H
δ5.4:d 1H
δ6.7–7.7:m 9H.

(B) Production of α-iodoethynyl-3-phenoxybenzyl-2,2-dimethyl-3-(2′,2′-dichloro-1′,2′-dibromoethyl)-cyclopropane-1-carboxylate A solution of 4.1 g of α-iodoethynyl-m-phenoxybenzyl alcohol in 20 ml of toluene is added dropwise to an ice-cooled solution of 4.5 g of 2,2-dimethyl-3-(2′,2′-dichloro-1′,2′-dibromoethyl)-cyclopropanecarboxylic acid chloride and 1.2 ml of pyridine in 50 ml of toluene. The reaction mixture is stirred under nitrogen for 16 hours at room temperature, and ether is then added. The ether extract is washed once with water, twice with 2 N hydrochloric acid and three times with saturated sodium chloride solution; it is subsequently dried over sodium sulfate, filtered, and concentrated by evaporation. The product is chromatographed through silica gel with ether/hexane (1:10) as the eluant to thus obtain the compound of the formula

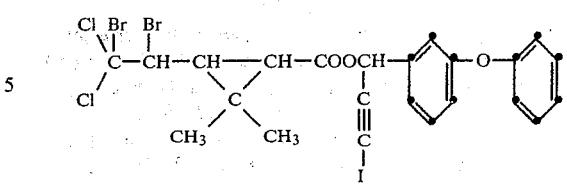

$n_D^{20°} = 1.5822$

The following compounds are obtained in an analogous manner:

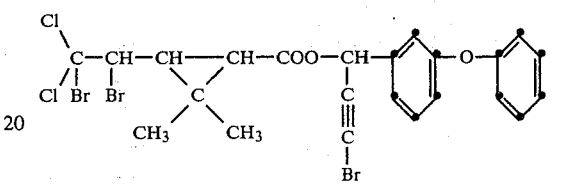

$n_D^{20°} = 1.5961$

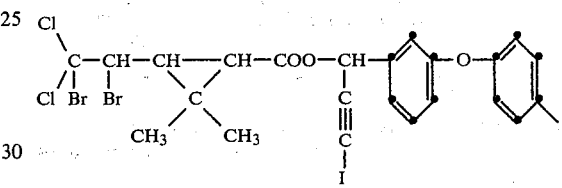

$n_D^{20°} = 1.5821$

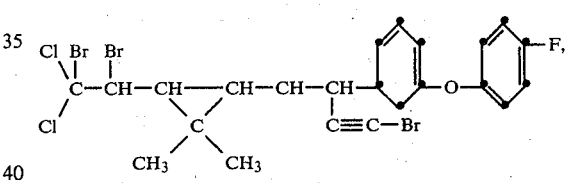

$n_D^{20°} = 1.5758$

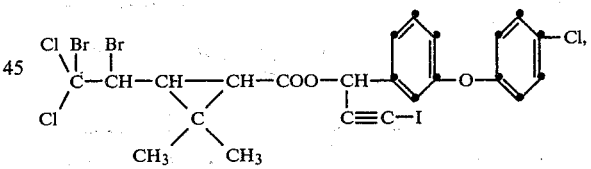

$n_D^{37°} = 1.6052$

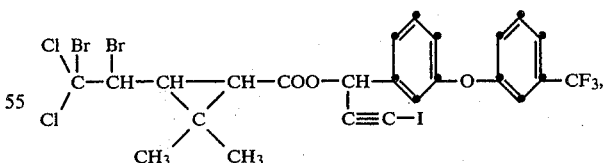

$n_D^{23°} = 1.5750$

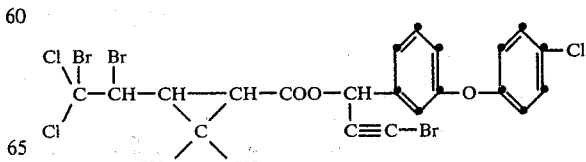

$n_D^{30°} = 1.5818$

-continued

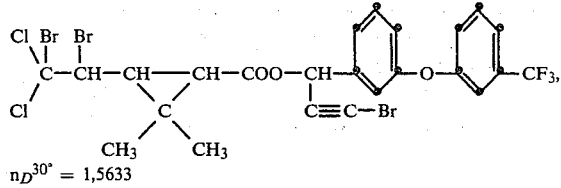

$n_D^{30°} = 1.5633$

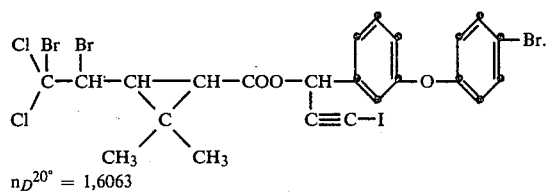

$n_D^{20°} = 1.6063$

EXAMPLE 2

Insecticidal stomach-poison action

Cotton plants were sprayed with aqueous active-substance emulsions or suspensions which contained 100, 200, 400 and 800 parts by weight, respectively, of active substance per $10^6$ parts by weight of additives, and which had been prepared in each case from one of the emulsifiable concentrates, wettable powders, granulates or sprays described in the formulation examples given in the foregoing. After the drying of the coatings, the cotton plants were infested with larvae of Spodoptera littoralis ($L_3$) and Heliothis virescens ($L_3$), respectively. The test was carried out at 24° C. with 60° C. relative humidity.

Compounds according to Example 1 exhibited in the above test a good insecticidal stomach-poison action against Spodoptera littoralis and Heliothis virescens larvae.

EXAMPLE 3

Acaricidal action

Leaf sections of Phaseolus vulgaris plants infested with Tetranychus urticae larvae were sprayed with aqueous emulsions which contained 100, 200, 400 and 800 parts by weight, respectively, of active substance per $10^6$ parts by weight of additives, and which had been prepared from one of the emulsifiable concentrates, wettable powders, granulates or sprays described in the formulation examples given in the foregoing. An assessment was made after two days with respect to the living and dead individuals, respectively, and the minimum concentration required to effect a 100% mortality rate was determined.

Compounds according to Example 1 were effective in the above test against adults, larvae and eggs of Tetranychus urticae.

EXAMPLE 4

(a) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks and in the case of the larvae after 2 days. There were two repeats for each test.

(b) *Boophilus microplus* (larvae)

With a dilution series analogous to that of Test (a), tests were carried out with 20 sensitive larvae and OP-resistant larvae, respectively (resistance is with respect to diazinon compatibility).

Compounds according to Example 1 were effective in these tests against adults and larvae of Rhipicephalus bursa and against sensitive and OP-resistant larvae, respectively, of Boophilus microplus.

| | Minimum concentration in parts by weight of AS per $10^6$ parts by weight of additives to effect a 100% mortality of | | |
|---|---|---|---|
| | *Spodoptera littoralis* larvae | *Heliothis virescens* larvae | *Tetranychus urticae* larvae |
| 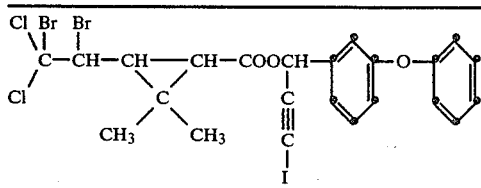 | 100 | 100 | 200 |
| 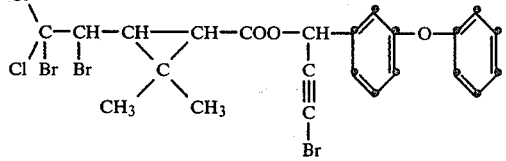 | 200 | 100 | 400 |
| 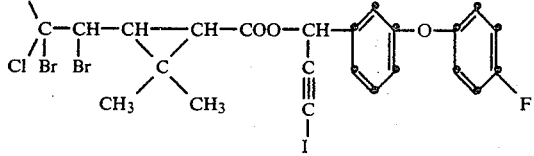 | 100 | 100 | 200 |

|  | Minimum concentration in parts by weight of AS per $10^6$ parts by weight of additives to effect a 100% mortality of | | |
|---|---|---|---|
|  | Spodoptera littoralis larvae | Heliothis virescens larvae | Tetranychus urticae larvae |
| [structure with Cl,Br,Br; C≡C—Br; F] | 100 | 200 | 200 |
| [structure with Cl,Br,Br; C≡C—I; Cl] | 100 | 200 | 200 |
| [structure with Cl,Br,Br; C≡C—I; CF₃] | 100 | 200 | 200 |
| [structure with Cl,Br,Br; C≡C—Br; Cl] | 200 | 200 | 400 |
| [structure with Cl,Br,Br; C≡C—Br; CF₃] | 200 | 200 | 400 |
| [structure with Cl,Br,Br; C≡C—I; Br] | 100 | 100 | 200 |
| PHENOTHRIN (NL Pat. Spec. No. 7,409,256) | 400 | 800 | 800 |

What is claimed is:

1. A compound of the formula

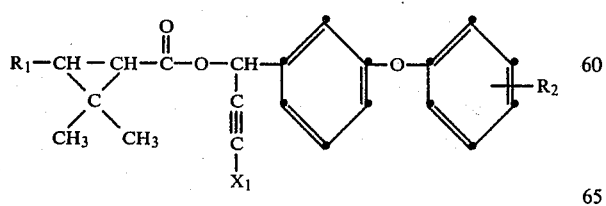

wherein
R₁ is

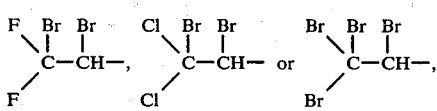

R₂ is hydrogen, fluorine, chlorine, bromine, methyl, trifluoromethyl or methoxy, and
X₁ is halogen.

2. A compound according to claim 1, wherein R₁ is

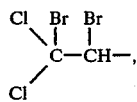

$R_2$ is hydrogen, fluorine, chlorine, bromine or trifluoromethyl, and $X_1$ is bromine or iodine.

3. A compound according to claim 2, wherein $R_2$ is hydrogen or fluorine.

4. The compound according to claim 3 of the formula

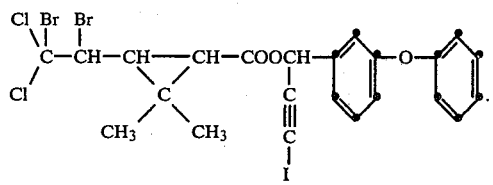

5. The compound according to claim 3 of the formula

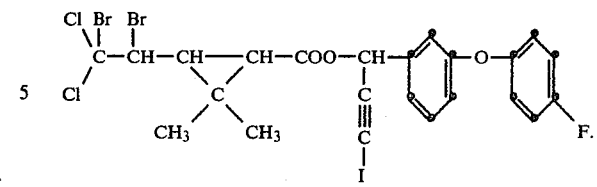

6. The compound according to claim 3 of the formula

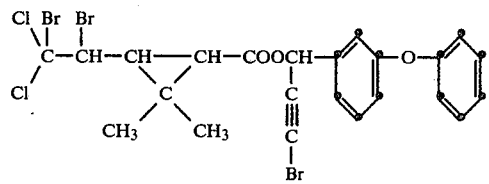

7. An insecticidal or acaricidal composition which comprises an insecticidally or acaricidally effective amount of a compound according to claim 1 as active ingredient, and suitable carriers.

8. A method of combating insects and acarids which comprises applying to the locus thereof an insecticidally or acaricidally effective amount of a compound according to claim 1.

* * * * *